(12) United States Patent
Christoudias

(10) Patent No.: US 6,176,866 B1
(45) Date of Patent: Jan. 23, 2001

(54) SCISSORS

(76) Inventor: George C. Christoudias, 17 Lower Cross Rd., Saddle River, NJ (US) 07548

(*) Notice: Under 35 U.S.C. 154(b), the term of this patent shall be extended for 0 days.

(21) Appl. No.: 09/163,212

(22) Filed: Sep. 29, 1998

Related U.S. Application Data

(60) Provisional application No. 60/065,258, filed on Nov. 20, 1997, and provisional application No. 60/067,164, filed on Dec. 4, 1997.

(51) Int. Cl.[7] .................................................. A61B 17/32
(52) U.S. Cl. ............................ 606/174; 606/167; 30/194
(58) Field of Search .................................. 606/167, 174, 606/205–211; 30/146, 194, 195, 223, 234, 244, 252

(56) References Cited

U.S. PATENT DOCUMENTS

| | | | |
|---|---|---|---|
| 714,087 | * 11/1902 | Woods | 30/194 |
| 874,847 | * 12/1907 | Hulse | 30/195 |
| 3,052,026 | * 9/1962 | Muller | 30/194 |
| 5,314,440 | * 5/1994 | Shapiro | 606/174 |

* cited by examiner

*Primary Examiner*—Glenn K. Dawson
(74) *Attorney, Agent, or Firm*—Richard A. Joel, Esq

(57) ABSTRACT

A scissor comprises a rigid blade with a fixed shape and an adjustable spring blade both pinned together at the end of the blade portions. The blades also comprise elongated leg portions extending outwardly from the junction with the blade portions and terminating in curved finger loops or a manipulating handle. The adjustable spring blade comprises a blade with spring like properties of the cutting edge which is continuously maintained in rotation around the fixed axis of the non-cutting edge of said rigid blade. When the scissors are open, the line of the cutting edge of the spring blade penetrates the plane of the opposing blade. This penetration stops when the scissors are closed. The rotation of the spring blade cutting edge may be clockwise or counter-clockwise but is always directed towards the sharp edge of the opposing blade of the scissors and thus continuously engages the sharp edge of the opposing blade at the cutting point.

5 Claims, 4 Drawing Sheets

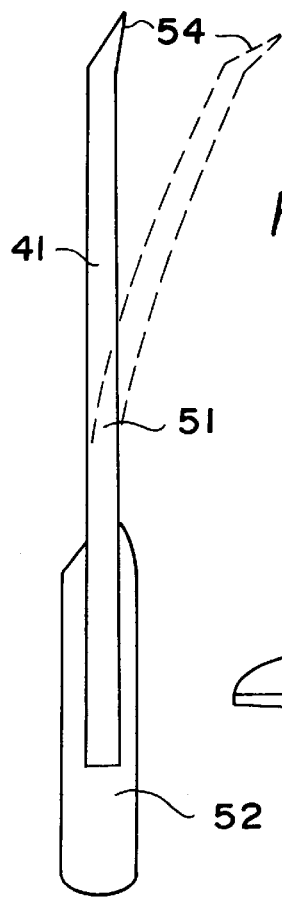
FIG. 2a
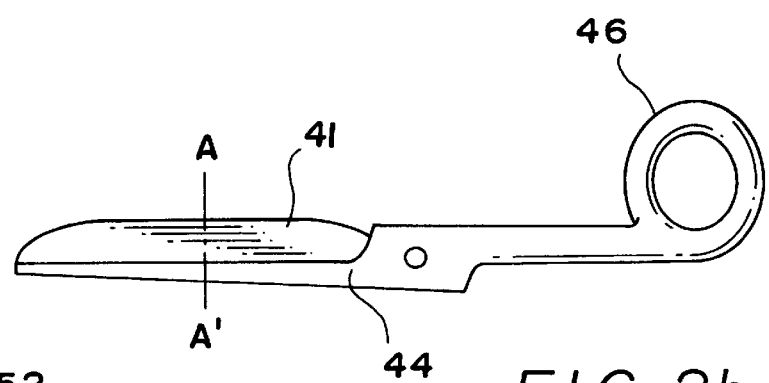
FIG. 2b
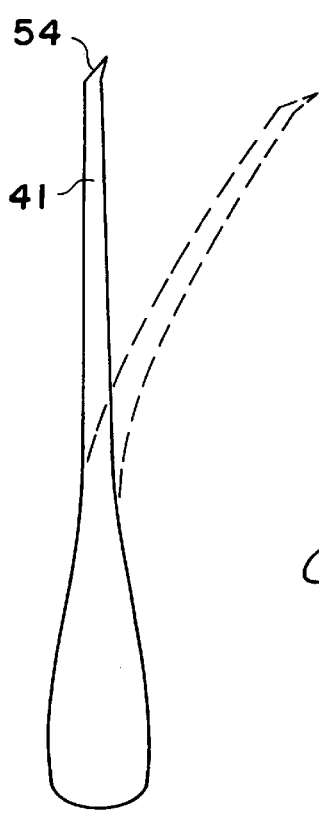
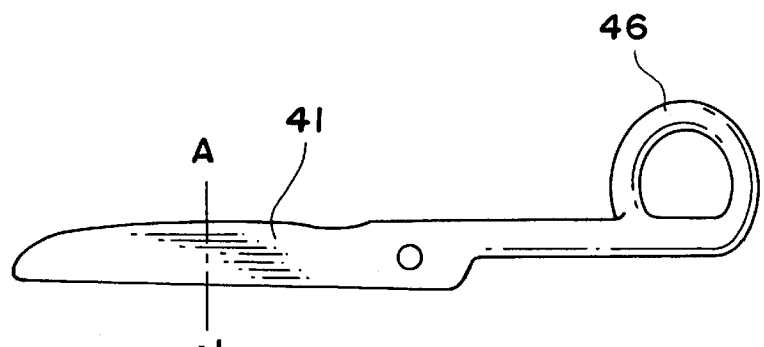
FIG. 2d
FIG. 2c

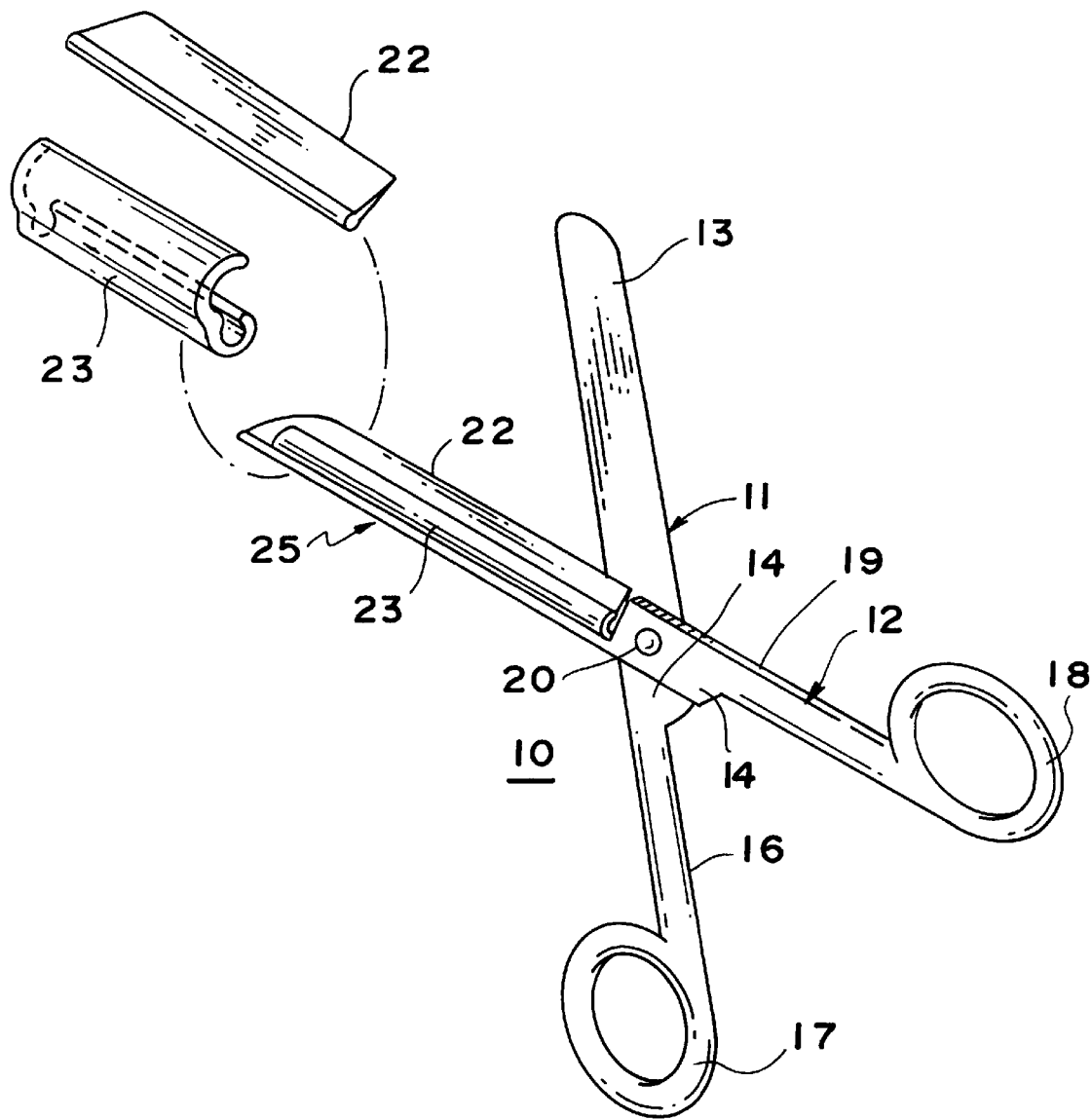

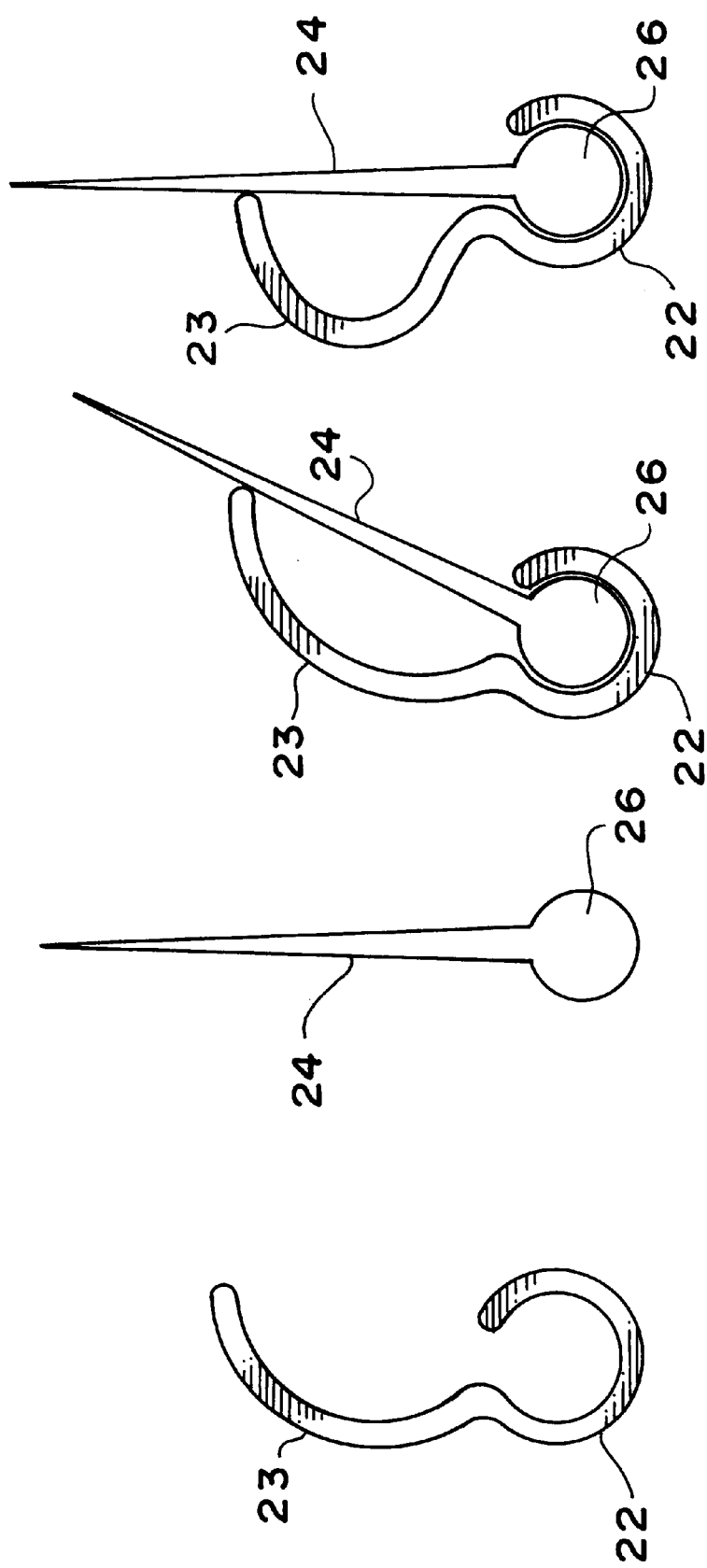

SCISSORS

This application claims benefit to U.S. Provisional No. 60/065,258 filed Nov. 20, 1997 and Ser. No. 60/067,164 filed Dec. 4, 1997.

BACKGROUND OF THE INVENTION

In the scissor art, it is necessary to maintain the blades in contact with one another so that a clean cut can be made. This applies to surgical scissors and conventional scissors as well. Over a period of time the blades may become loose at the hinge point causing the blade surfaces to disengage and cause a ragged or incomplete cut. Another problem develops when the blades become warped and contact between the opposing surfaces for cutting is uneven. Finally, the blades themselves become dull and ineffective after use. This dullness may be remedied periodically by having the scissors sharpened but there is a cost involved and the scissors are out of service during the interval. More importantly, dull blades can be dangerous and fail to perform the expected task which is to provide a precise clean cut.

The prior art includes U.S. Pat. No. 5,320,636 to Slater on endoscopic scissors with cammed surface end effectors; U.S. Pat. No. 5,314,440 on a microsurgical scissor apparatus; and, U.S. Pat. No. 5,395.386 to Slater on endoscopic pericardial scissors.

Special use surgical scissors are disclosed in U.S. Pat. Nos. 5,275,607; 5,219,354; 5,591,173; 5,002,554; 5,346,500; and, 5,275,607.

Bipolar electrical scissors are shown in U.S. Pat. Nos. 5,658,281; 5,514,134; 5,540,685; and, 5,569,243.

Other patents of general interest include U.S. Pat. Nos. 5,531,755; 5,569,298; 5,556,407; and, 5,583,845. None of the foregoing patents discloses the unique scissors proposed in this application.

In addition to the patents cited above, the prior art is the conventional scissor and variations thereof. Applicant has invented a new and improved scissor called the EVER-CUTT™ which maintains the blades in contact and provides a strong torque to facilitate cutting. A spring and mobile blade assembly maintains the mobile and stationary blades in contact so that the edges provide a clean shearing cut. Furthermore, the spring urged mobile blade includes a twisted edge which facilitates contact with the edge of the opposing blade and minimizes the need for sharpening.

In addition, the continuous contact of the blades at the cutting edge renders the scissors ambidextrous since they function equally well whether operated by a left handed or right handed person. It is not believed that similar scissors exist having the unique design and advantages stated herein.

SUMMARY OF THE INVENTION

This invention relates to scissors and particularly to a new and improved scissors wherein a mobile spring blade is maintained in constant contact with a rigid blade for cutting purposes.

A scissor comprises a rigid blade with a fixed shape and an adjustable spring blade both pinned securely together at the end of the blade portions. The blades also comprise elongated leg portions extending outwardly from the junction of the blade portions and terminating in curved finger loops or a manipulating handle. The adjustable spring blade comprises a blade with spring like properties of the cutting edge which is continuously maintained in rotation around the fixed axis of the non-cutting edge of said rigid blade.

When the scissors are open, the line of the cutting edge of the spring blade penetrates the plane of the opposing blade. This penetration stops when the scissors are closed.

In said embodiment, the rotation of the spring blade cutting edge may be clockwise or counter-clockwise but is always directed towards the sharp edge of the opposing blade of the scissors and thus continuously engages the sharp edge of the opposing blade at the cutting point. Furthermore, the fixed axis of the non-cutting edge of the spring blade and the cutting edge of the stationary blade cross each other during use forming a variable angle. When the scissor is closed, the axis of the non-cutting edge of the spring blade is parallel to the axis of the non-cutting edge of the rigid blade. The cutting edge of the spring blade penetrates the plane formed by these axes so that when the scissors are activated, the cutting edge of the rigid blade and the cutting edge of the spring blade come into contact at only one point. With the scissors open, a certain point of the base of the cutting edge of each blade is in contact with a corresponding point of the base of the other cutting edge. The tip of the cutting edge of the spring blade lies beyond the plane formed by the axis of the cutting and non-cutting edges of the fixed blade and the axis of the non-cutting edge of the spring blade as the scissors are closed. The previous point of contact of the sharp edge of the spring blades moves away from the plane so that the line of the cutting edge of the spring blade ceases to penetrate the plane of the stationary blade when the scissors are in a closed position.

In an alternate embodiment, the scissors comprise a first conventional limb having a blade cutting portion at one end and an intermediate lever portion terminating in a finger loop. The cooperating limb with the mobile blade is hinged to the first blade at a point between the blade and the lever portion. The mobile blade is mounted to a spring and frame at one end which are attached to a lever portion of the limb terminating in a finger loop. In one embodiment, the mobile blade may be detachable from the aforementioned assembly.

The spring urges the mobile blade into constant contact under pressure with the stationary blade for cutting purposes. The mobile blade portion has a slight twist at its edge to effectuate the improved blade contact which is limited to the cutting edge only. Not only does this design result in an optimum cut with a higher torque, but the blades rarely need sharpening. The scissors are particularly useful in conventional and laparoscopic surgery and in any situation when a clean precise cut is needed.

A further embodiment involves the use of two opposing spring blades which bring additional pressure to bear at the cutting edge.

Accordingly, it is an object of this invention to provide a new and improved scissors having a spring blade.

Another object of this invention is to provide a new and improved surgical scissor having a rigid blade and a cooperating spring blade which penetrates the plane of the rigid blade when open to provide a continuous variable cutting point as the scissors is closed.

Another object of this invention is to provide a new and improved scissors wherein a spring blade is twisted at its edge to maintain engagement with the opposing rigid blade during cutting.

A further object of this invention is to provide a new and improved scissors wherein one of the cutting blades is engaged by spring means to maintain contact with the opposing blade.

A still further object of this invention is to provide a new an improved surgical scissors having a pair of adjustable spring blades which cooperate at a cutting point as the blades are closed.

Another object of this invention is to provide a new and improved scissors with ambidextrous qualities which produces a reliable and predictable cut.

A more specific object of this invention is to provide a new and improved scissors having a conventional blade engaged by a mobile blade having a twisted spring urged edge to maintain pressured contact with the conventional blade for superior cutting.

BRIEF DESCRIPTION OF THE DRAWINGS

The above and other objects and advantages of this invention may be more clearly seen when viewed in conjunction with the accompanying drawings wherein:

FIG. 2 is a side view of the flexible blade;

FIG. 2a is an exaggerated cross-sectional view of the flexible spring sheet metal blade shown in FIG. 2b. The flexible blade 41 is shown in a closed position and in an open position in phantom;

FIG. 2b shows a side view of a flexible blade;

FIG. 2c depicts a side view of the spring blade with FIG. 2d showing a cross-section of the blade 41 through line A—A, the flexible blade 41 is shown in a closed position in FIG. 2d and in phantom in an open position;

FIG. 3a discloses a view of the scissors with the two sections of the blade shown separately in FIG. 3b; and FIGS. 4a–4c show the spring in FIG. 4a and the mobile blade in FIG. 4b. FIG. 4c depicts the mobile blade in place with the scissors open while FIG. 4d depicts the mobile blade in place with the scissors closed.

DETAILED DESCRIPTION OF THE INVENTION

Figures 1A, 1B, 1C:
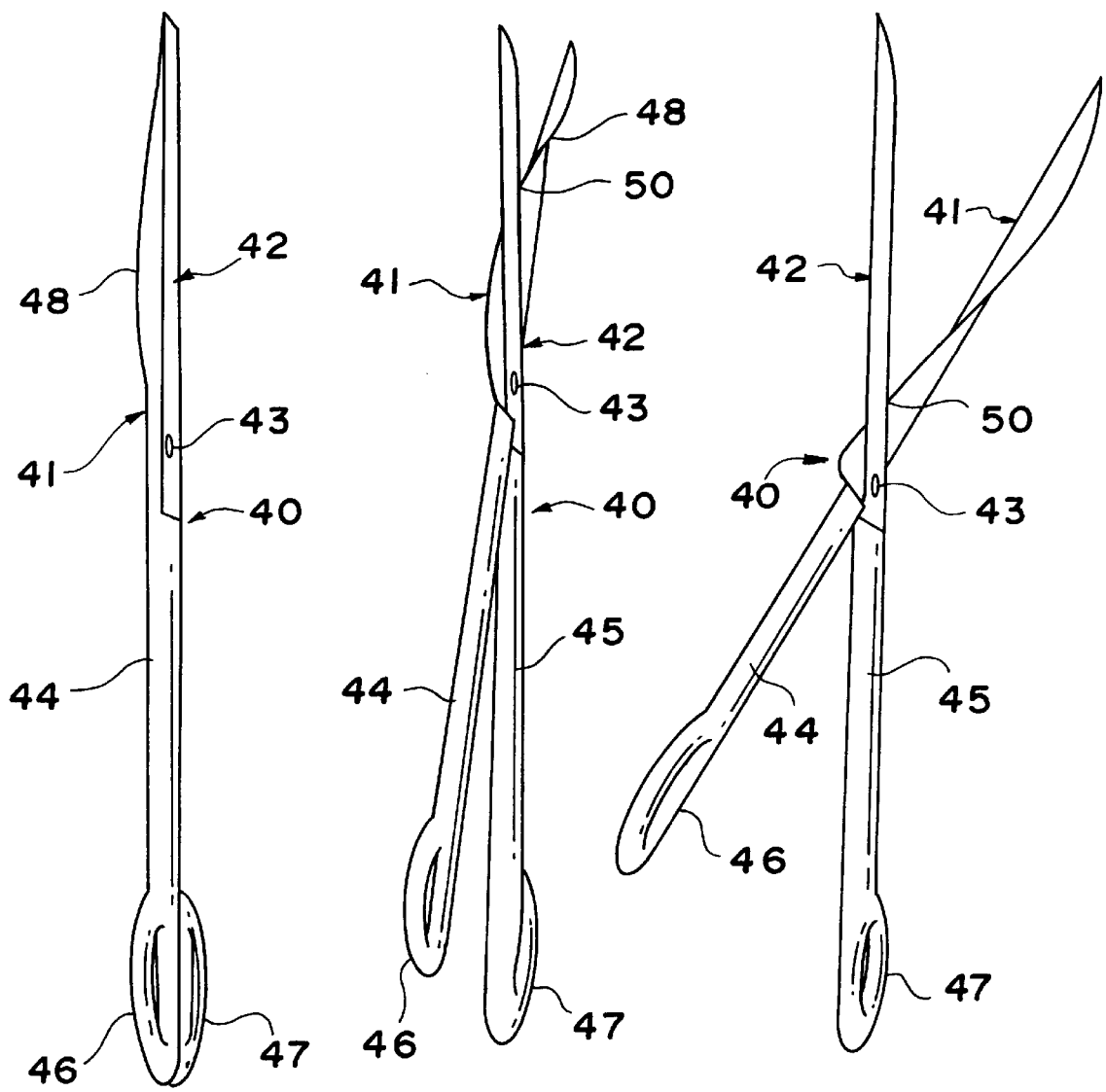
FIG. 1a is a view of the mobile spring blade crossing the plane of the stationary blade with the finger loops closed.
FIG. 1b is a view of the mobile spring blade crossing the plane of the stationary blade at the cutting point with the scissors in use.
FIG. 1c is a view of the mobile spring blade and the stationary blade at the variable angle as the scissors are open prior to cutting.

Referring now to the drawings, FIG. 1a discloses a scissor 40 having a mobile spring blade 41 and a stationary blade 42 pinned at 43 and having elongated limbs 44 and 45 terminating in finger loops 46, 47. In FIG. 1b, the sharp edge 48 of the spring blade 41 penetrates the plane formed by the stationary blade 42 to effect a, cutting point 50 where the blades 41, 42 come in contact. FIG. 1c depicts the blades 41 and 42 in an open position with the dull edge 49 of the stationary blade on the outside and the sharp edge 48 of the mobile spring blade 41 on the inside. In effect, FIG. 1c depicts the scissors 40 ready for operation, FIG. 1b depicts the scissors 40 in use and FIG. 1a depicts the scissors 40 after use.

FIG. 2a is an view of a cross-section of of the spring blade 41 taken along the line A—A of FIG. 2b in an open position in phantom and in a closed position elongated portion of flexible spring sheet metal 51 having a rigid base portion 52 which is part of the non-flexible frame 44. A cutting edge 54 is located at the end of the spring blade 41. The blade 41 is shown in phantom in the open A side view of the flexible blade 41 is shown in FIG. 2b. Alternatively, the spring sheet metal blade 41 could have a rigid blade (not shown) with the cutting edge 54 at its extremity. FIG. 2c illustrates a further embodiment of the scissors 40 with the spring blade 41 in an open in phantom while FIG. 2d is a cross-section of the blade 41 through the section A—A.

In use, the mobile spring blade 41 crosses over the plane of the stationary blade 42 as shown in FIG. 1b and stops when the scissors are closed as shown in FIG. 1a. The spring blade 41 penetrates the aforesaid plane at the point of contact 50 between the respective cutting edges providing considerable shearing pressure. The blades 41 and 42 rest in a substantially parallel position when the scissors 40 are closed.

Referring now to FIG. 3a and 3b the invention in another embodiment, comprises a scissor 10 having a limb 11 with a, "stationary" blade and a limb 12 with a mobile blade. The limb 11 includes the blade portion 13, a central hinge portion 14 and an elongated lever portion 16 having a finger loop 17 at the end 52 thereof. The limb 12 also includes a finger grip or loop 18 at one end and a lever portion 19 extending upwardly to the hinge 20. The blade portion 21 of limb 12 comprises a frame 22 and spring 23 and a detachable blade 24 which is mounted to the frame 22.

The blade portion of limb 12 is shown in FIG. 4a–4c with the blade portion 24 slidably mounted to the frame 22. FIGS. 4a, 4b and 4c depict the frame 22 and blade 24 assembly wherein the spring 23 is in contact with the blade 24. FIG. 4d illustrates a slight twist in the blade portion 24 which maintains the cutting point of blade portion 24 in contact with the opposing blade portion 13. FIG. 5b shows the blade portion 24 with the tip of the blade edge higher than the base of the cutting edge 25 due to the twisting action on the blade 24. When the edge 25 is opposed to the stationary blade 11, the base 26 of the blade portion 24 will be twisted counterclockwise away from the stationary blade portion 13. The separation between the base of the blades will be greater when the tip 27 of the mobile blade is meeting with the corresponding tip of the stationary blade. In an ordinary scissor, the cutting edge of both blades are parallel or in the same plane.

In the invention as just described, the scissor 10 includes cutting edges which are always in contact at one point under pressure. This keeps the edges sharp and provides a clean sharp cut. The scissors 10 may be used in conventional surgical procedures and with the appropriate modifications in laparoscopic surgery. They can also be used for all common purposes that: conventional scissors are currently used for. The scissors provide a high degree of efficiency with minimum effort in the foregoing uses.

In the embodiments of FIGS. 1 and 2, the blade portion 24 is spring metal and is always pushing against the stationary blade 13 to effect a cutting action. This design eliminates the need for a separate spring 23 and a separate blade with a consequent cost savings.

While the invention has been explained by a detailed description of certain specific embodiments, it is understood that various modifications and substitutions can be made in any of them within the scope of the appended claims which are intended also to include equivalents of such embodiments.

What is claimed is:

1. A scissors comprising:
   a rigid blade having a cutting blade portion at one end and an elongated portion at the other end wherein said cutting blade and elongated portion are joined at an intermediate point;
   an adjustable spring blade having a spring blade portion at one end including a cutting edge having a twist along its entire length which adjusts relative to the rigid blade to engage the cutting blade portion thereof, a cutting point formed by said engagement and an elongated portion at the other end wherein said spring blade portion and elongated portion are joined at an intermediate point;

means rotatably pinning said blades together and; wherein, said blades extend for a predetermined distance in an opposed relationship and wherein said elongated portions include control means at the end thereof.

2. A scissors-in accordance with claim 1 wherein:

the spring blade portion comprises a flexible spring sheet metal portion at one end joined to the elongated portion of said adjustable spring blade, and said cutting edge being non-flexible.

3. A scissors in accordance with claim 1 wherein:

the spring blade comprises an elongated flexible spring sheet metal portion wherein the cutting edge is sharp and the rigid blade includes a sharp edge along the cutting blade portion to cooperate with the cutting edge of the adjustable spring blade.

4. A scissors in accordance with claim 1 wherein:

the control means comprises finger loops.

5. A scissors in accordance with claim 1 wherein:

the position of said blades causes constant contact at the cutting point of the blades permitting ambidextrous operation in opening and closing of said scissors.

\* \* \* \* \*